United States Patent [19]
Bryson et al.

[11] Patent Number: 5,328,646
[45] Date of Patent: Jul. 12, 1994

[54] AIR FLOW CONTROL SYSTEM WITH REPLACEABLE CARTRIDGE

[75] Inventors: John D. Bryson, Milwaukee; John D. Bryson, Jr., Pewaukee, both of Wis.

[73] Assignee: Vaportek, Inc., Sussex, Wis.

[21] Appl. No.: 137,655

[22] Filed: Oct. 15, 1993

[51] Int. Cl.⁵ .............................................. B01F 3/04
[52] U.S. Cl. ...................................... 261/52; 261/102; 261/DIG. 65
[58] Field of Search ................. 261/52, 102, DIG. 65

[56] References Cited

U.S. PATENT DOCUMENTS

| | | | |
|---|---|---|---|
| 3,298,674 | 1/1967 | Gilbertson | 261/52 |
| 3,785,556 | 1/1974 | Watkins | |
| 3,874,146 | 4/1975 | Watkins | |
| 3,885,737 | 5/1975 | Watkins | 239/34 |
| 3,923,934 | 12/1975 | Watkins | 261/52 |
| 4,059,657 | 11/1977 | Hay | 261/DIG. 65 |
| 4,271,092 | 6/1981 | Sullivan et al. | 261/102 |
| 4,370,300 | 1/1983 | Mori et al. | 261/102 |
| 4,377,399 | 3/1983 | Bryson | 261/52 |

OTHER PUBLICATIONS

Vaportek Brochure "The Optimum 1000 Environmental Odor Controller".

*Primary Examiner*—Tim Miles
*Attorney, Agent, or Firm*—Quarles & Brady

[57] ABSTRACT

An air treatment system has a removable and replaceable cartridge, the cartridge having a cylindrical plastic canister, and having a liquid-permeable vaporizing element disposed in the canister. The canister is located on one side in a cradle inside a housing where air flow is controlled between inlet and outlet ports by a pivoting frame member. A slider is moved up and down outside the housing to simultaneously move a pair of arms inside the housing into closed, partially open or fully open positions relative to the inlet and outlet ports. The canister has ports of special configuration and a baffle is placed in the canister to assist radial air flow and assure that air flows over the coiled air vaporizing element.

16 Claims, 3 Drawing Sheets

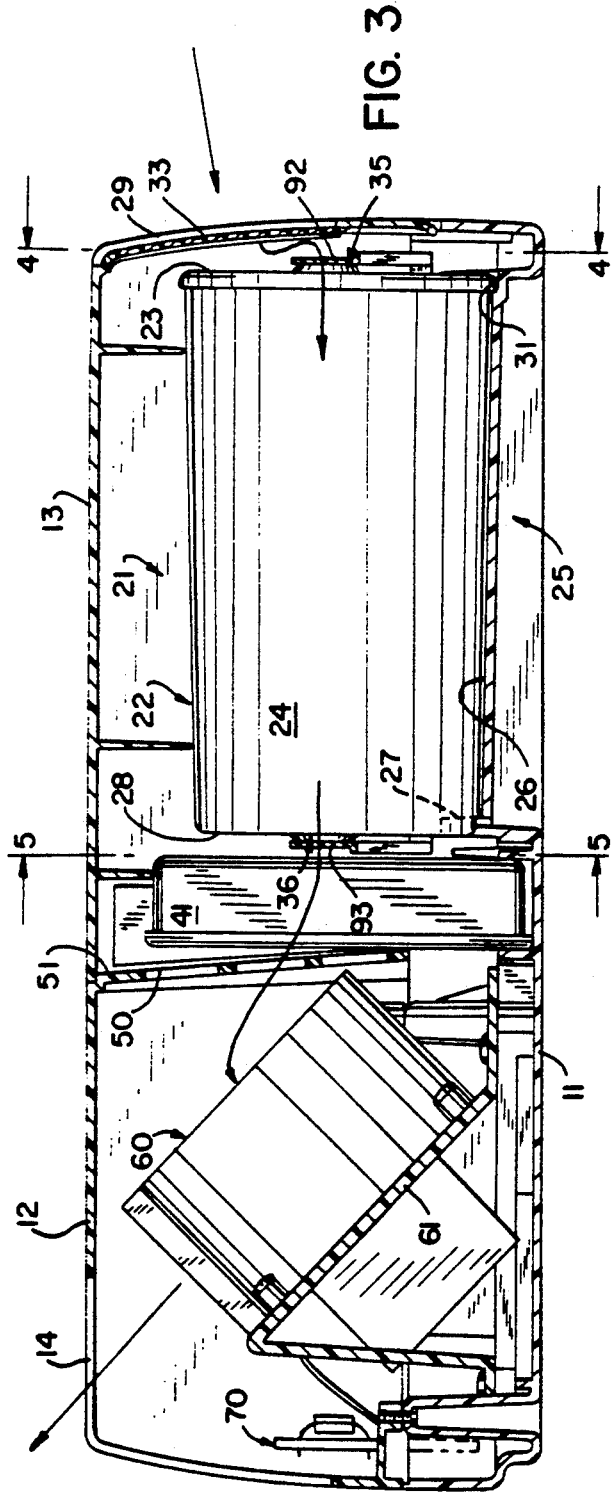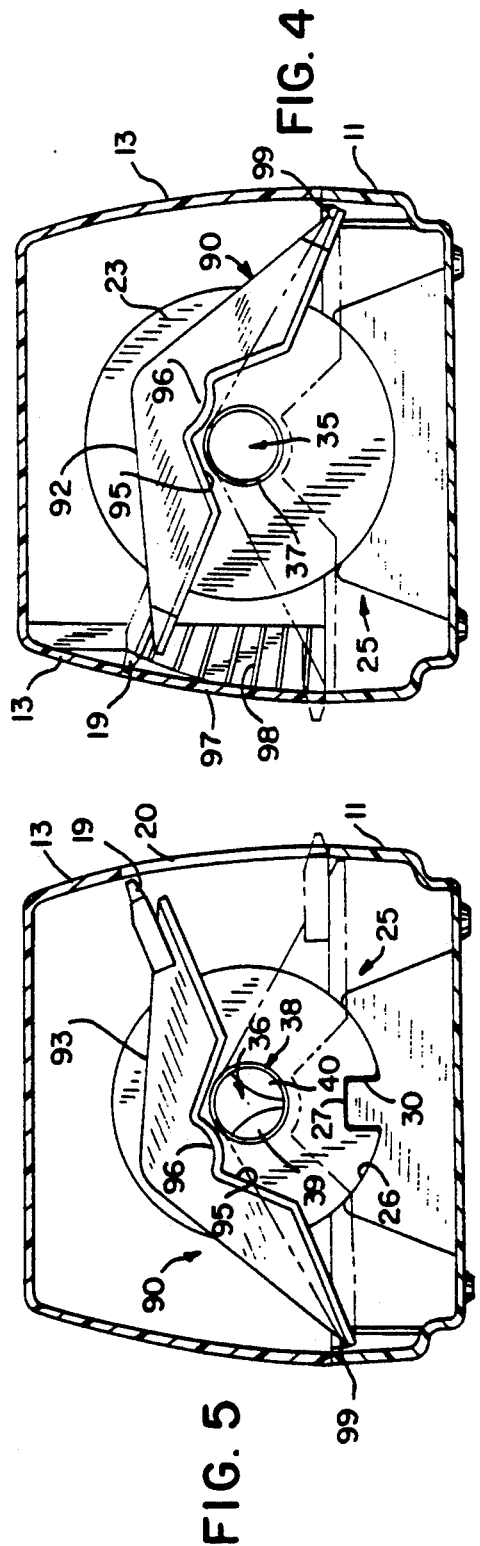

AIR FLOW CONTROL SYSTEM WITH REPLACEABLE CARTRIDGE

TECHNICAL FIELD

The invention relates to small, portable vaporizing equipment for dispensing liquids into the air to improve the quality of the air.

BACKGROUND ART

Various types of vaporizing apparatus have been known for treating air. Watkins, U.S. Pat. No. 3,923,934, issued Dec. 2, 1975, shows a device for vaporizing a liquid into the air to control odors. Such a device is more broadly applicable to the dispensing of liquids, including odorants, deodorants, and air fresheners.

The Watkins device includes a chamber in which a liquid is vaporized by passing air through a coiled, corrugated element. The liquid is sealed within ridges in the corrugated element, which is described in further detail in Watkins, U.S. Pat. No. 3,885,737, issued May 27, 1975.

In the Wilkins '934 patent, an inlet port in a front wall of the chamber communicates with a central tube formed by the element along its longitudinal axis when the element is coiled. An outlet port is also provided in the front wall of the chamber, radially outward from the inlet port. A disc-shaped shutter is rotated to simultaneously control the opening of the inlet and outlet ports on the front side of the air flow chamber.

Air is circulated first through the inlet port and the central tube in the coiled element. It then passes radially outward, and is then drawn back through the coiled element and out of the outlet port to be mixed with air from the outside. The vapor is then blown outside the unit by a motorized fan.

In this prior device, the air flows through a somewhat complex path, and the control mechanism has many parts. It would be beneficial to provide a more efficient air flow control mechanism, that could be manufactured at lower cost.

Replacement of the vaporizing element in the Watkins unit was not as convenient as desired. This was improved in a later version by providing a replaceable cartridge in a cylindrical canister. To replace the cartridge, a housing end plate was removed and the cartridge was inserted into a housing chamber. In this version, positioning of the inlet and outlet ports in the front end or top of the cartridge could not be easily observed, because the front end was inserted first into the housing chamber.

SUMMARY OF THE INVENTION

The invention relates to methods and apparatus for improved air flow and air flow adjustment through the vaporizing element. The invention also relates to improved construction of a replaceable cartridge for an air treatment system.

The air treatment system of the invention includes a canister with an inlet port and outlet port located in opposite end walls of the canister, a cradle for supporting the canister in a lying-down position substantially parallel to an external supporting surface for the air treatment system, a housing cover for the air treatment system that can be moved between a closed position and an open position to expose the cradle for removal and replacement of the canister thereon, and an air flow control mechanism having a pair of arms spaced longitudinally relative to the canister and crossing the inlet and outlet ports, respectively, the pair of arms being pivotable around an axis substantially parallel to a longitudinal axis of the canister to move between a first position simultaneously closing the inlet and outlet ports and a second position simultaneously opening the inlet and outlet ports.

This air flow control system provides for air flow from one end of the cartridge to the other. It also provides a system that has cost advantages over the prior systems.

An air treatment cartridge of the invention includes inlet and outlet ports of a particular configuration, in which the outlet port is defined by two arcuate webs forming a V-shaped opening with arcuate edges. Peripheral lips are provided around the inlet port and outlet port for assisting in closure of the ports by the arms of the control mechanism.

The air treatment cartridge also advantageously includes a means for securely locating the cartridge on the cradle. A cover at one end provides a lip for locating one end of the cartridge on the cradle, while the opposite end of the cartridge forms a keyway for locating the cartridge both longitudinally and rotationally in the air treatment system.

The invention has thus provided an air treatment cartridge that is more convenient to use and replace in the above-described air flow control system.

Other objects and advantages, besides those discussed above, will be apparent to those of ordinary skill in the art from the description of the preferred embodiment that follows. In the description, reference is made to the accompanying drawings, which form a part hereof, and which illustrate examples of the invention. Such examples, however, are not exhaustive of the various embodiments of the invention, and, therefore, reference is made to the claims which follow the description for determining the scope of the invention.

BRIEF DESCRIPTION OF THE DRAWINGS

FIG. 3 is a left side view of the interior of the apparatus of FIG. 1, showing an air flow control system and replaceable cartridge of the present invention;

FIG. 4 is a front end view taken in the plane indicated by line 4—4 in FIG. 3; and FIG. 5 is a rear end view of the air flow control and cartridge taken in the plane indicated by line 5—5 in FIG. 3;

DETAILED DESCRIPTION OF THE PREFERRED EMBODIMENT

Figure 1:
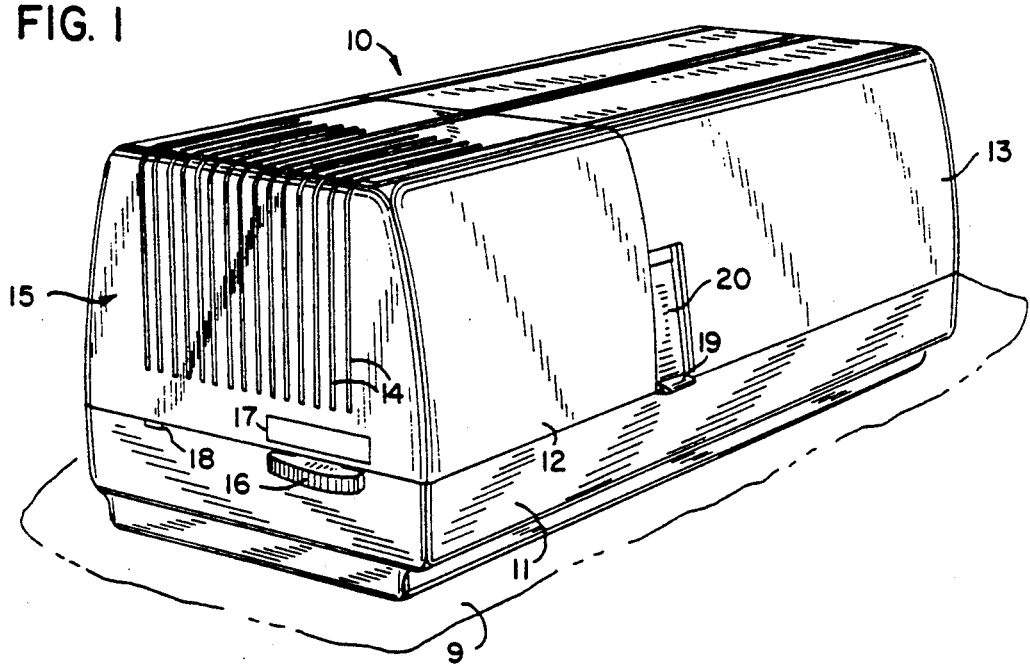
FIG. 1 is a right side perspective view of an apparatus incorporating the present invention.

FIG. 1 shows an air treatment system 10 that incorporates the present invention. The apparatus 10 includes an exterior housing having three main parts: a base or chassis 11, a front end cover 12 and a rear end cover 13. The chassis 11 is supported by external supporting surface 9. The front end cover 12 includes spaced parallel vents 14 forming a grille 15 for venting vaporized air into the environment. On the front side of cover 12 is a blower switch member 16, which is slideable left and right to several switch positions represented by legend 17. These positions select the following functions (ON, OFF, HI SPEED, etc.). Also, on the front side of cover 12, to the left in FIG. 1 is an LED 18, for indicating certain conditions to the user.

The rear cover 13 is pivotable at the rear end, so as to open the rear portion of the housing for access to the inside. An access button (not shown) on the hidden left side of the housing must be operated, before the rear cover 13 can be pivoted upward. FIG. 1 also shows an air flow control member 19 on the right that slides up and down in a slot 20 formed between the front cover 12 and the rear cover 13 of the housing.

Referring next to FIG. 3, a replaceable cartridge 21 is disposed on its side. The cartridge 21 includes a canister 22 with a disc-shaped cover 23 and a cylindrical bottom member 24, the cover 23 facing towards vents 29 formed at the rear end of the apparatus 10 (FIG. 3).

Figure 2:
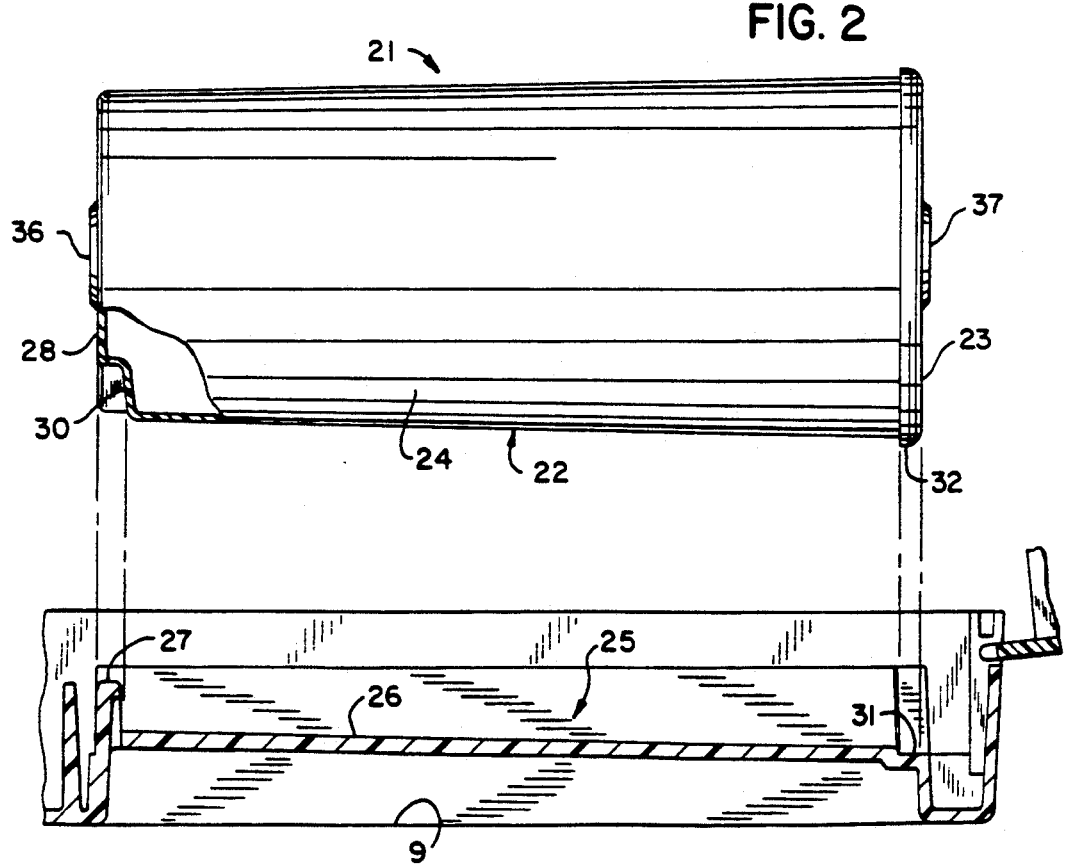
FIG. 2 is an enlarged, left side detail view of a replaceable cartridge seen in FIG. 3.

The canister 22 is supported in a longitudinal trough 26 (FIGS. 2, 5) within a cradle 25 that is formed as an integral part of the chassis 11. The cradle 25 also forms an upstanding rectangular key 27 (FIG. 5) near the middle of the housing 11, 12, 13, as seen in FIGS. 2 and 3. This key 27 is used to locate the bottom end wall 28 of the cartridge 21, which has a rectangular keyway 30 (FIGS. 2, 5) for receiving the key 27 and locating the canister 22 longitudinally and rotationally in the cradle 25. At an opposite end of the cradle 25 is a transverse, arcuate depression 31 (FIG. 2) for receiving and supporting the lip 32 formed by the cartridge cover 23. The cradle 25, and locating means at each end, aid in the convenient replacement of a used cartridge 21 with a new cartridge. As a result of replacing the entire cartridge 21, an air treatment element within the canister 22 need not be handled.

Whereas, the front grille 15 extends on the front and part of the top side of the front cover 12, the rear grille has a number of parallel vents 29 (FIG. 3), similar to front vents 14. The rear grille 15 stops approximately where the top face meets the rear face of the rear cover 13. As seen in FIG. 3, a filter element 33 is mounted in channels integrally formed with the rear cover 13 just inside the rear vents 29.

As illustrated in FIG. 3, by the arrows, untreated air flows in through rear vents 29 and filter 33 into inlet port 35 in the cartridge cover 23. Vapor-laden air flows out of an outlet port 36 at the other end of the canister 22. The vapor-laden air then flows through a filter assembly 41 and vents 50 in a rear wall 51 of the front housing cover 12, the air being drawn by the suction created by a fan 60. The fan 60 is mounted in an inclined position on support 61. The fan 60 exhausts vapor-laden air at an upward angle through the front grille 15. A circuit board 70 carrying electronic circuitry is mounted on edge near the front of the housing. This circuitry 70 controls the fan motor 60 in response to operation of the switch 16 seen in FIG. 1. The circuitry on circuit board 70 is also connected to user signaling devices, such as the LED 18 on the front and a sound device (not shown). The circuitry is also part of a filter and cartridge replacement sensing system, which is more fully described in a copending application entitled "Filter Sensing System" filed on even date herewith and assigned to the assignee of the present invention.

Figure 7:
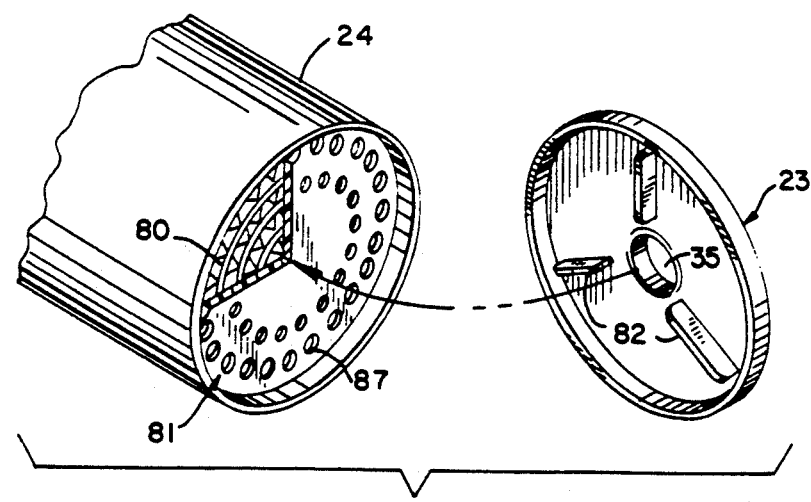
FIG. 7 is a partially exploded detail view of the cartridge of FIGS. 2-6.

FIG. 7 shows details of the cartridge 21 including the canister cover 23, the canister bottom member 24, the coiled vaporizing element 80 and a baffle 81.

The canister cover 23 includes three integrally formed ribs 82 (FIG. 7), disposed 120° apart, to provide radial air passageways from the inlet port 35. Three similar ribs 83 (FIG. 6) are formed on an inside bottom of the bottom member 24. The ribs 82 direct air flow radially outward from inlet port 35, and through the outer layers of element 80. Ribs 83 direct the air radially inward to outlet port 36.

The vaporizing element 80 (FIGS. 6 and 7) is the same as that described in U.S. Pat. No. 3,885,737, cited above. The element 80 is made of a plastic material and contains two parallel plies with transverse, corrugated ridges 84 running parallel to each other. The plies act to seal in a quantity of air treatment liquid which may be a deodorant, an odorant, or another liquid to be vaporized in the air. There are also some longitudinal ridges traversing the transverse ridges 84 to prevent the transverse ridges 84 from nesting when the element 80 is wound in a coil. For further description, the relevant description in U.S. Pat. No. 3,885,737, cited above, is incorporated herein by reference.

An air baffle 81 contains holes 86, 87 of increasing size arranged in two concentric rings located at respective radial distances from the center of the disk. The baffle 81 acts to diffuse air from the inlet port 35 into parallel streams for passage over layers of the coiled vaporizing element 80. The plastic material of the vaporizing element 80 is permeable by the liquid contained therein, while the walls of the canister 22 are impermeable by the same liquid. Thus, as air passes over the vaporizing element 80, the air treatment liquid is evaporated into the air flow. The amount of evaporation is a function of air flow.

Figure 6:
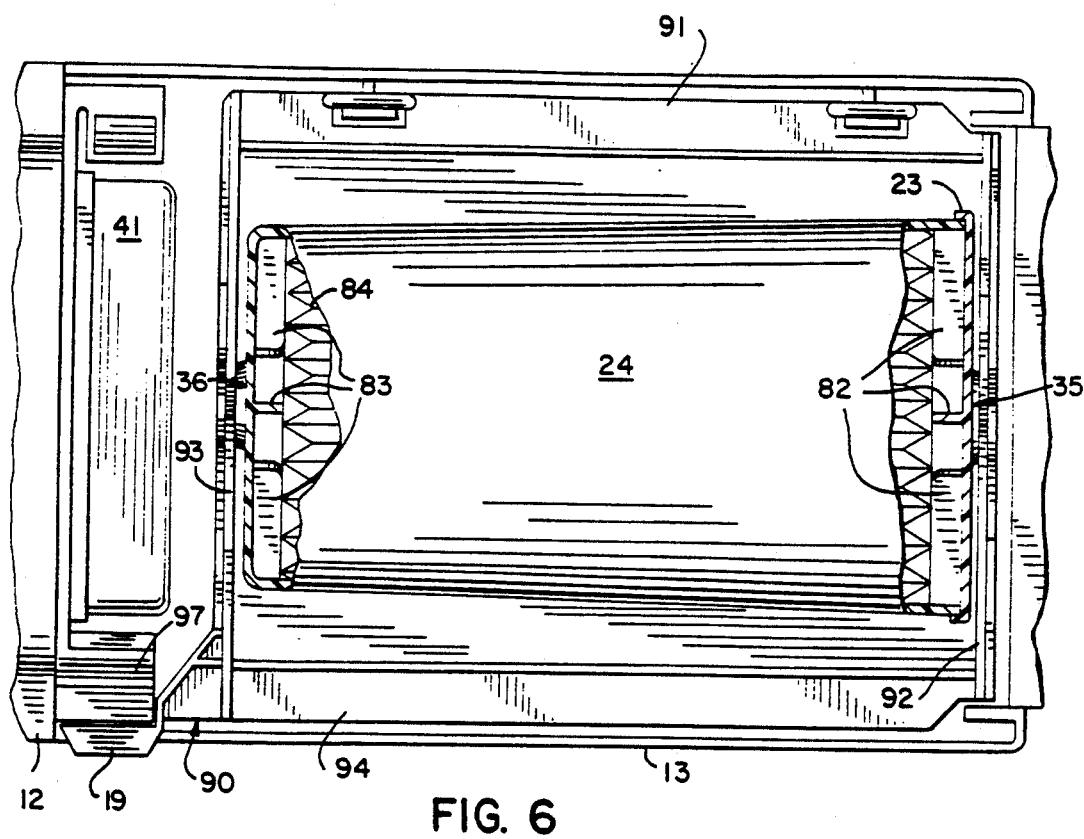
FIG. 6 is a top view of the air flow control and cartridge of FIG. 2 with parts broken away.

The invention provides an improved and more convenient control of air flow in the form of a slider 19 integrally formed with a pivotable frame member 90 as seen in FIG. 6. The frame member 90 is pivoted along a first cross member 91, also seen in FIG. 6, which connects two air flow control arms 92, 93 (FIGS. 4, 5). The control arms 92, 93 are connected on an opposite side by a second cross member 94 seen in FIG. 6, and the slider 19 extends from one end of this member 94 through a narrow space between the front cover 12 and rear cover 13 (FIG. 1), so that the slider 19 is placed in slot 20, where it moves up and down.

Referring next to FIG. 4, the cartridge inlet port 35 is a round hole in the center of the cover 23 that has a lip 37 around its periphery. The cartridge outlet port 36 also has a circular peripheral lip 38, however, the cartridge outlet port 36 is reduced from circular to approximately a V-shape by arcuate webs 39, 40 formed within the peripheral lip 38. The top of the outlet port 36 is bounded by an arcuate portion 40 of the lip 58.

The control arms 92, 93 (FIGS. 4, 5) are generally the shape of an isosceles triangle with a low peak and two long equal sides running to the respective cross members 91, 94. Each triangular arm has a recess 95 large enough to uncover its respective port 35, 36 when the base radius of the control arm 92, 93 lies across the center of the respective port 35, 36. Within this recess is an arcuate web 96, which will close over all or a portion of each port 35, 36, while maintaining a crescent shape for the inlet port 25 and the V-shape for the outlet 36 in all partially open positions.

During operation, the slider 19 (FIGS. 1 and 6) is lifted from its lowermost position (shown in phantom in FIGS. 4 and 5) corresponding to fully closed ports to an uppermost position (shown in full in FIGS. 4 and 5) corresponding to fully open ports. Between these two extremes, there are a plurality of partially open positions corresponding to slide positions along a ratchet formed on an abutment 97 extending from the rear of the front cover 12. The slide 19 acts as a pawl, which can be moved and lodged on one of the ridges 98 forming the ratchet on the abutment 97. The ridges 98 are formed along radial lines running through an axis of rotation 99 for the slider-frame member 90.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

I claim:

1. An air treatment system of the type having a portable cartridge with a cylindrical canister, having a liquid-containing and liquid-permeable air treatment element disposed in the canister, and the canister having walls, including opposite end walls, that are impermeable to liquid from the air treatment element, wherein the air treatment system further comprises:
   the canister having an inlet port and outlet port located in the opposite end walls of the canister;
   a cradle for supporting the cylindrical canister in a lying-down position substantially parallel to an external supporting surface for the air treatment system;
   a housing cover for the air treatment system that can be moved between a closed position and an open position to expose the cradle for removal and replacement of the canister thereon; and
   an air flow control mechanism having a pair of arms spaced longitudinally relative to the canister and crossing the inlet and outlet ports, respectively, the pair of arms being pivotable around an axis substantially parallel to a longitudinal axis of the canister to move between a first position simultaneously closing the inlet and outlet ports to a second position simultaneously opening the inlet and outlet ports.

2. The air treatment system of claim 1, wherein the air flow control mechanism includes a portion extending outside the housing for manual operation of the air flow control mechanism.

3. The air treatment system of claim 1, wherein
   the cradle forms a key projecting upward at one end of the cradle; and
   wherein the canister bottom forms a keyway for receiving the key and locating the cartridge both longitudinally and rotationally in the cradle.

4. The air treatment system of claim 1, wherein the canister includes a lip at one end and wherein the cradle forms a depression at an end opposite the key for receiving the lip of the canister and assisting longitudinal location of the canister.

5. An air treatment cartridge of the type for installation in an air treatment system, the cartridge having a cylindrical canister, having a liquid-containing and liquid-permeable air treatment element disposed in the canister, and the canister having walls, including opposite end walls, that are impermeable to liquid from the air treatment element, and wherein the air treatment cartridge further comprises:
   a cover forming one of the opposite end walls of the canister, the cover having an inlet port therein for receiving air into the canister;
   another of the opposite end walls having an outlet port to allow air flow out of the canister;
   wherein the inlet port is circular with a peripheral lip that is contacted by a first closure when the inlet port is partially or fully closed;
   wherein the outlet port has a circular peripheral lip that is contacted by a second closure when the outlet port is partially or fully closed; and
   wherein the outlet port is defined by two arcuate webs that form a V-shaped opening having arcuate edges.

6. The air treatment cartridge of claim 5, further comprising:
   an air diffuser element including holes disposed radially from a center of the air diffuser element, the air diffuser element being positioned in the canister between the lid and the air treatment element to diffuse air from the center of the canister radially outward and through the holes prior to passage of the air in the longitudinal direction through the canister and the air treatment element.

7. The air treatment cartridge of claim 5, wherein the air diffuser elements has holes of two sizes positioned in two respective rings at two respective radial distances from the center of the air diffuser element.

8. The air treatment cartridge claim 5, which further comprises a plurality of radial ribs inside the cover and inside the opposite end wall of the canister to allow radial air flow at the respective ends of the canister.

9. The air treatment cartridge claim 5, wherein the canister bottom forms a keyway for receiving a key projection within the air treatment system to locate the cartridge both longitudinally and rotationally in the air treatment system.

10. The air treatment cartridge claim 9, wherein the keyway is rectangular in shape.

11. An air treatment cartridge of the type for installation in an air treatment system, the cartridge having a cylindrical canister, having a liquid-containing and liquid-permeable air treatment element disposed in the canister, and the canister having walls, including opposite end walls, that are impermeable to liquid from the air treatment element, wherein the air treatment cartridge further comprises:
   a cover forming one of the opposite end walls of the canister, the cover having an inlet port therein for receiving air into the canister, and the cover having means for locating one of the opposite end walls relative to a support in the air treatment system;
   another one of the opposite end walls having an outlet port to allow air flow out of the canister;
   the one of the opposite end walls having the outlet port also forming a keyway for receiving a key projection within the air treatment system to locate the cartridge both longitudinally and rotationally in the air treatment system.

12. The air treatment cartridge of claim 11, wherein the keyway is rectangular in shape.

13. The air treatment cartridge claim 11, which further comprises a plurality of radial ribs inside the cover and inside of the other one of the end walls of the canister to allow radial air flow at the respective ends of the canister.

14. The air treatment cartridge of claim 11, further comprising:

an air diffuser element including holes disposed radially from a center of the air diffuser element, the air diffuser element being positioned in the canister between the cover and the air treatment element to diffuse air from the center of the canister radially outward and through the holes prior to passage of the air in the longitudinal direction through the canister and the air treatment element.

15. The air treatment cartridge of claim 14, wherein the air diffuser elements has holes of two sizes positioned in two respective rings at two respective radial distances from the center of the air diffuser element.

16. The air treatment cartridge claim 11, wherein the inlet port is circular with a peripheral lip that is contacted by a first closure when the inlet port is partially or fully closed;

wherein the outlet port has a circular peripheral lip that is contacted by a second closure when the outlet port is partially or fully closed; and wherein the outlet port is defined by two arcuate webs reducing the outlet port opening to a V-shaped opening having arcuate edges.

* * * * *